(12) United States Patent
Hendren et al.

(10) Patent No.: US 6,959,590 B2
(45) Date of Patent: Nov. 1, 2005

(54) EMISSION SAMPLING APPARATUS AND METHOD

(75) Inventors: Fredrick Hendren, Hull (CA); Bruce Ainslie, Hull (CA)

(73) Assignee: Her Majesty The Queen in Right of Canada as represented by the Minister of the Environment, Ottawa (CA)

(*) Notice: Subject to any disclaimer, the term of this patent is extended or adjusted under 35 U.S.C. 154(b) by 0 days.

(21) Appl. No.: 10/276,640

(22) PCT Filed: May 24, 2001

(86) PCT No.: PCT/CA01/00746

§ 371 (c)(1),
(2), (4) Date: Nov. 19, 2002

(87) PCT Pub. No.: WO01/90741

PCT Pub. Date: Nov. 29, 2001

(65) Prior Publication Data

US 2003/0136177 A1 Jul. 24, 2003

Related U.S. Application Data

(60) Provisional application No. 60/206,802, filed on May 25, 2000.

(51) Int. Cl.⁷ ..................... G01M 19/00; G01N 33/497
(52) U.S. Cl. ..................... 73/118.1; 73/23.32; 73/23.31
(58) Field of Search ............ 73/23.31, 23.32, 73/118.1

(56) References Cited

U.S. PATENT DOCUMENTS

| | | | |
|---|---|---|---|
| 2,734,381 A | * | 2/1956 | Jacobson .............. 73/196 |
| 3,406,562 A | * | 10/1968 | Perna, Jr. et al. .......... 73/23.31 |
| 4,633,706 A | * | 1/1987 | Ito et al. ................ 73/23.33 |
| 5,058,440 A | | 10/1991 | Graze |
| 5,129,257 A | | 7/1992 | Carduner et al. |
| 5,639,957 A | | 6/1997 | Zarchy |
| 5,968,452 A | | 10/1999 | Silvis |
| 6,062,092 A | | 5/2000 | Weaver |
| 2002/0166393 A1 | * | 11/2002 | Dageforde ................ 73/864 |

FOREIGN PATENT DOCUMENTS

| EP | 428850 A1 | * | 9/1990 | |
| JP | 7035660 A | * | 2/1995 | |
| WO | WO 98/13680 | * | 4/1998 | ........ 73/23.31 |

OTHER PUBLICATIONS

Japan Abstract, vol. 1997, No. 10JP 09 145562 A Jun. 6, 1997 (Hino Motors Ltd.).

EP 0428 850 (Mitsubishi Motors Corp.) May 29, 1991.

* cited by examiner

Primary Examiner—Michael Cygan
(74) Attorney, Agent, or Firm—McFadden, Fincham

(57) ABSTRACT

A self contained field sampling system for measuring engine exhaust emissions includes a mini-dilution tunnel adapted for the collection of proportional samples of emissions to be analyzed, an engine air intake flow measurement instrument, a system controller and data acquisition system, and an optionally portable generator to provide electrical power. Several probes withdraw dilute and undiluted exhaust for emission analysis. Various engine emissions may be isolated. As well, engine emissions mass rate may be calculated by reference to engine RPM, inlet flow rate, exhaust temperature and emissions output rate.

21 Claims, 3 Drawing Sheets

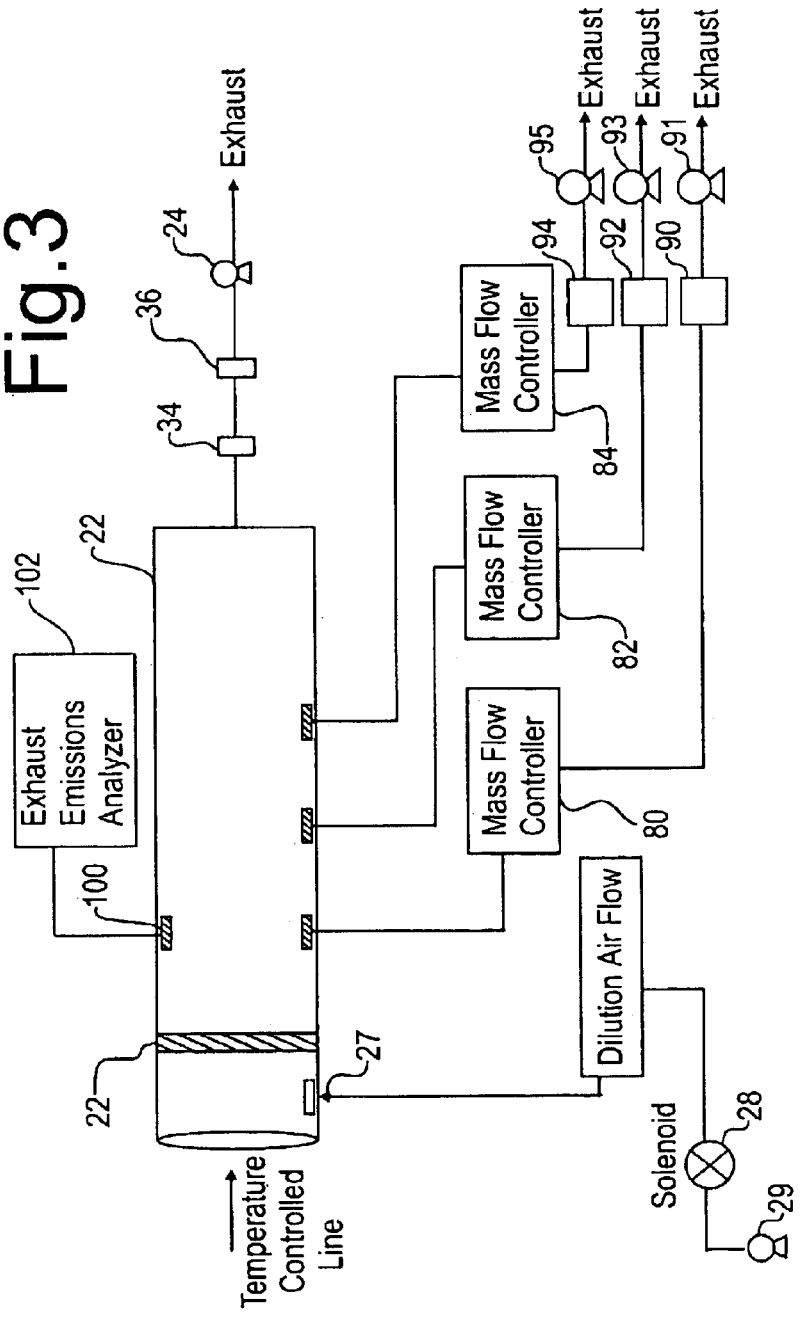

EMISSION SAMPLING APPARATUS AND METHOD

This is a national phase application of International publication WO 01/90741 (PCT/CA01/00746), filed on May 24, 2001, which claims priority to U.S. provisional patent application 60/206,802, filed May 25, 2000.

BACKGROUND OF THE INVENTION

1. Field of the Invention

The present invention relates to engine emission sampling for emissions characterization, emissions control technology verification, vehicle maintenance and other purposes. In particular, the invention pertains to a self-contained transportable unit for sampling exhaust emissions from vehicles and other sources both mobile and stationary.

2. Description of the Prior Art

Current environmental requirements often require investigators to conduct representative exhaust emissions data from motor vehicles and other emissions-generating sources such as remote power generating plants and the like. Often, such testing is done at locations which are remote from a testing lab. This requires a readily portable sampling and analysis system. This equipment must effectively provide the same results as laboratory equipment consisting of a metered proportional volume sampling system and analysis system. The vehicle chassis dynamometer system found in a conventional emissions lab, is replaced by simply operating the vehicle under operational loads. The vehicle emissions then have to be measured to determine mass emission rates as per the laboratory system.

It is desirable to provide a portable system that has the capability to conduct the field testing as noted above. Therefore there is a need for a portable sampling system for the continuous measurement of exhaust emissions in a self-contained unit which may be attached to a vehicle for on-road testing or to any other emissions source.

Within the prior art, there are disclosed various systems for field sampling of exhaust emissions. For example, U.S. Pat. No. 4,586,367 by Louis et al., discloses an apparatus for measuring the particulate and/or gaseous content of exhaust emissions. The apparatus connects to a vehicle tailpipe and directs a portion of the affluent into a dilution chamber, downstream of which emissions contents are measured. U.S. Pat. No. 5,090,258 to Yamaski et al., discloses an analyzer which samples a portion of engine exhaust emission.

U.S. Pat. No. 5,410,907 to Ström et al., discloses an engine exhaust pipe sampler for measuring engine exhaust gases. The gases are directed into a dilution tunnel which directs a portion of the diluted exhaust gas into various analyzers. A central processor measures fuel flow and carries out various analyses.

U.S. Pat. No. 6,085,582 by Tripathi, et al. discloses an apparatus for measuring vehicle exhaust mass emissions comprising an exhaust inlet for collecting vehicle exhaust, a dilution air inlet connected with exhaust inlet to provide a diluted vehicle exhaust. A first analyzer which measures concentration of undiluted exhaust, a second analyzer which measures concentration of diluted exhaust, a meter which measures flow rate of dilute exhaust and a computer.

A particular requirement in this field is to provide for accurate measurement of emissions notwithstanding great variations in exhaust outflow. For example, a typical vehicle may vary greatly in its emissions between its idle phase, cruising, and acceleration or other heavy load modes of operation. Similarly, point emission sources such as generators can similarly vary in their emissions outflow. It is thus desirable to provide for a highly accurate means for measurement exhaust emissions, whilst still providing a readily transportable unit.

Potential applications for an emissions sampling apparatus and method of the general type characterized by this invention, includes a wide variety of exhaust emissions from both mobile sources and stationary sources. Mobile sources includes on and off road and non-road mobile sources, such as rail locomotives, boats, airplanes and equipment for use in construction, industrial, agricultural, mining and marine applications. Stationary sources includes electricity generators, power turbines and industrial equipment. Further, emissions may be sampled from a variety of gas, diesel or alternative-fuelled internal combustion engines as well as fuel cell technologies and micro turbines. The above listing is intended only to be representative of various applications, and not limiting of the invention in any respect.

SUMMARY OF THE INVENTION

According to one aspect of the present invention, there is provided a self contained field sampling system unit comprising an emissions dilution chamber which can be characterized as a mini-dilution tunnel, adapted for the collection of proportional samples of emissions to be analyzed, an emissions analyzer for regulated emissions, an air flow measurement instrument, a computer and data acquisition system, and a portable generator to provide electrical power.

The present invention may be used to replace the standard proportional volume sampling system (referred to as the CVS) normally found in vehicle exhaust emissions testing laboratories and light duty vehicle inspection and maintenance (I/M) emissions stations. In combination with a portable dynamometer and analysis bench, a complete portable exhaust emissions system may be provided. This portability provides the flexibility for testing engines in a variety of non-conventional locations, including remote road side locations.

For non-road applications such as locomotives and marine vessels, the system is preferably placed "on board" in proximity to the engine, with a probe mounted to the exhaust stack for sampling exhaust emissions during operation of the engine. Engine data such as fuel consumption is obtained from onboard instrumentation or the installation of the pertinent meters in order to determine mass emissions.

In one aspect, the invention consists of a portable self-contained system for sampling and analysing engine exhaust emissions of a mobile or stationary emission source in which the system has an inlet pipe for receiving an emission sample; a dilution tunnel having a plurality of sampling probes; within the dilution tunnel for withdrawing controlled volumes of diluted engine exhaust upstream from the dilution tunnel; emissions analysing means downstream of the tunnel, a control means for introducing dilution air into the tunnel, a sampling probe upstream of the dilution tunnel in operative association with the control means. The invention is characterized over the art by air inlet measuring means measuring air inlet flow rate into an engine, a plurality of pump means with which to draw a sample of the diluted engine exhaust through the probe means, and control means comprising a variable controller for controlling the volume of dilution air of the exhaust in inverse proportion to the ratio of engine air inlet flow rate and the engine inlet air flow rate at engine idle. Preferably, the engine air inlet measuring means comprises laminar flow elements. The apparatus is preferably housed in a convenient housing or is otherwise transportable to a remote location.

Multiple dilution tunnels may be provided.

The invention may further include a plurality of sampling probes within said dilution tunnel for withdrawing controlled volumes of diluted engine exhaust.

Further, the control means is preferably arranged for controlling the flow rate of dilution gas in inverse proportion to the ratio of engine air inlet flow rate and the engine inlet air flow rate at engine idle.

The control means preferably includes means for integrating data over an engine cycle ranging from idle to full engine load. The data may include emissions mass number or average emissions mass rate, engine air inlet flow rate, exhaust temperature, and engine RPM.

The invention may further include a sampling probe upstream of said dilution tunnel for withdrawing a controlled sample of undiluted engine exhaust.

The system is intended to include means for collecting and concentrating a plurality of emission samples for measuring specific emissions selected from one or more of:

THC;
CO;
$NO_x$;
$CO_2$;
aldehydes;
ketones;
semi-volatile organic compounds;
volatile organic compounds;
PAH;
n-PAH; and, The system may also include means for performing modal analysis on the engine exhaust, including providing a continuous emission monitor connected to one of the probes linked to the controller and calculating in the controller an emissions mass rate per second or an integrated emissions rate.

Desirably, the control means further comprises means for integrating data over an engine cycle of an engine ranging from idle to full engine load, the data comprising emissions mass number or average emissions mass rate, engine air inlet flow rate, exhaust temperature, and engine RPM, and the system further comprises means for collecting and concentrating emission samples with sampling media selected from one or more of: TEDLAR™ bag; 2, 4-DNPH prepared cartridge; TENAX™ cartridge; and, polyurethane foam. It is further desirable the volume of exhaust drawn from the emission source is varied, the volume being varied by the mass air flow rate controller at the exit of the tunnel or the volume of dilution air directed into the tunnel.

In another aspect, the invention consists of a method for sampling and analysing engine exhaust emissions from a stationary or mobile emission source in a portable self-contained system having a volume of exhaust drawn from the emission source, including the steps of:

connecting the portable self-contained system to the mobile or stationary emission source;

drawing a portion of engine exhaust emissions into a dilution tunnel upstream from the dilution tunnel during operation of the emission source; characterized by:

measuring the air intake flow rate from an engine during operation;

diluting the engine exhaust emissions in inverse proportion to the ratio of engine air inlet flow rate of the engine during an analysing event and engine air inlet flow rate of the engine during idle;

collecting samples of the diluted exhaust emission with a plurality of sampling probes; and, analysing emission mass rates for one or more emission component being measured Preferably the above aspect further comprises measuring and recording parameters selected from one or more of: engine inlet mass air flow rate, engine exhaust temperature, engine RPM, engine torque, and speed, and further comprises analysing one or more of continuous mass number, average emissions mass rate, engine air inlet flow rate, exhaust temperature, and engine RPM during operation of the emission source, and also further comprises sampling diluted exhaust with a plurality of probes each having an inlet within the dilution tunnel and delivering diluted exhaust samples to a plurality of collection media for concentrating selected emission components.

It is preferable the above aspect further comprises measuring emission components selected from one or more of:

THC;
CO;
$NO_x$;
$CO_2$;
aldehydes;
ketones;
semi-volatile organic compounds;
volatile organic compounds;
PAH;
n-PAH; and,
particulates.

In any of the above aspects it is desirable the volume is varied by the mass air flow rate controller at the exit of the tunnel and/or the volume of dilution air directed into the tunnel.

The invention may also comprise sampling diluted and optionally also undiluted exhaust with a plurality of probes each having an inlet within said dilution tunnel and delivering diluted exhaust samples to a plurality of sampling media for concentrating selected emission components.

BRIEF DESCRIPTION OF THE DRAWINGS

FIG. 3 schematically illustrates several of the components of the invention.

DETAILED DESCRIPTION OF THE PREFERRED EMBODIMENTS

Figure 1:
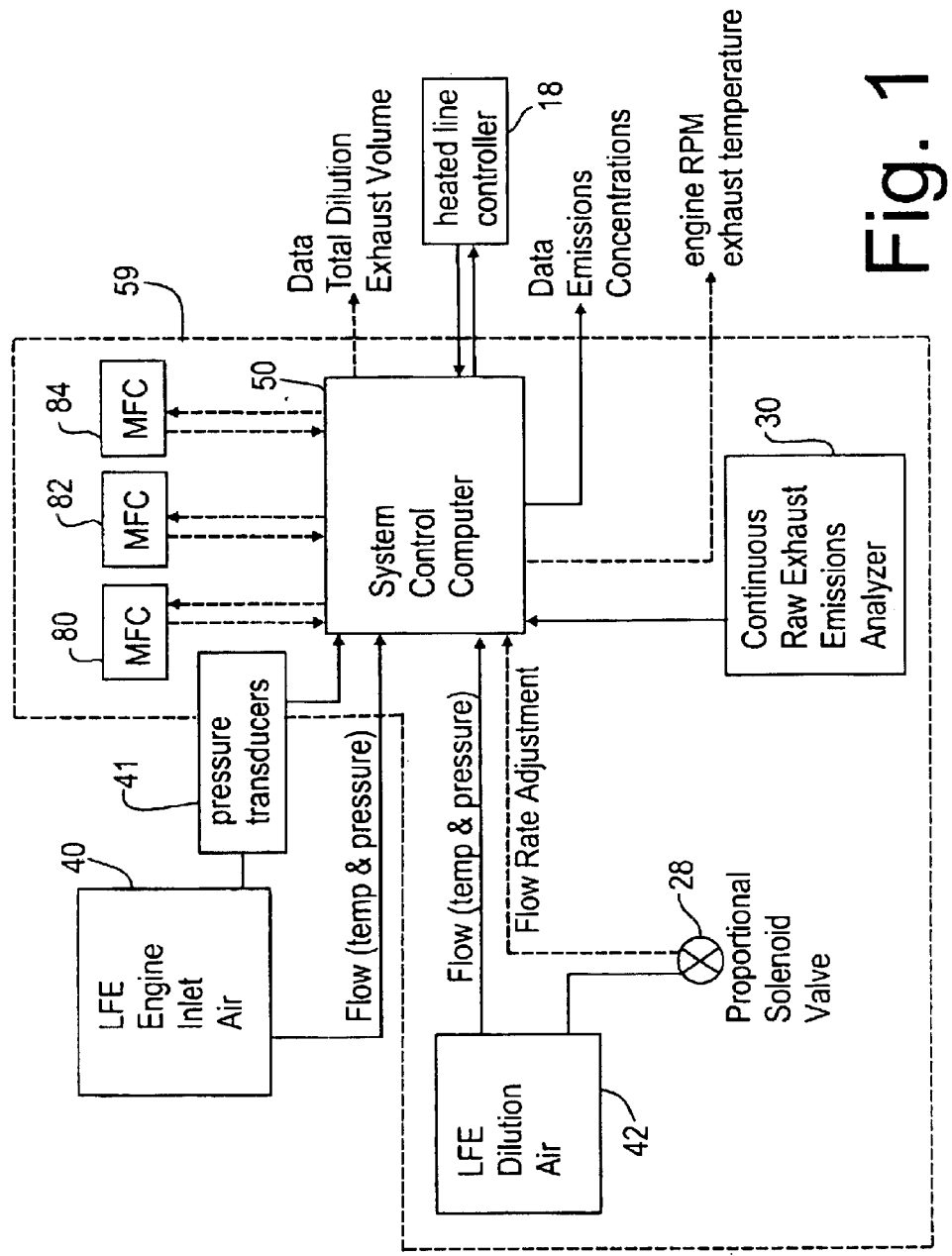
FIG. 1 is a schematic illustration of the logic control system of the present invention.
Figure 2:
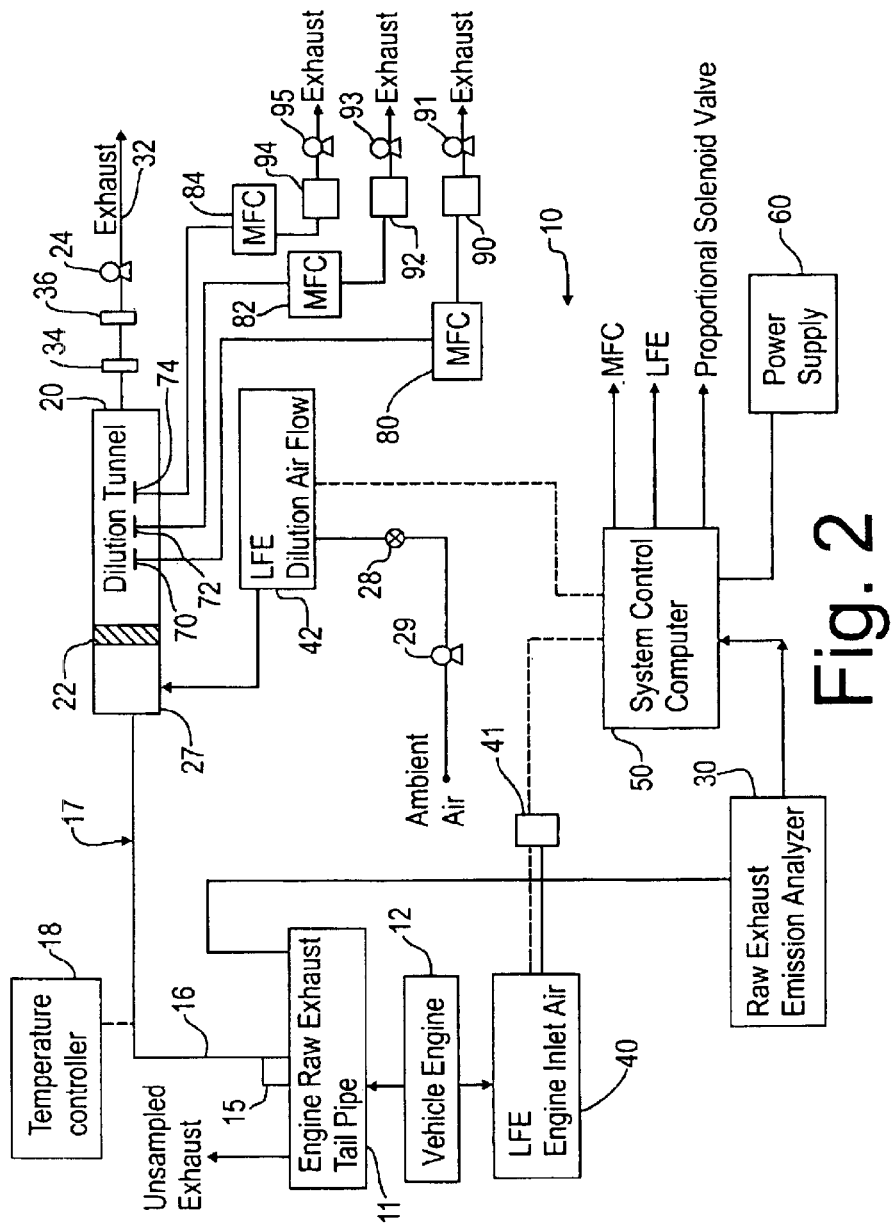
FIG. 2 is a schematic illustration of the present invention.

In a preferred embodiment of the invention, seen schematically at FIGS. 1 and 2, the sampling system 10 is a self contained unit consisting in general terms of an exhaust dilution chamber 20 or tunnel for the collection of proportional samples, an emissions analyzer 30 for regulated emissions, an air flow measurement instrument 40, a computer and data acquisition system 50 and optionally a portable generator to provide electrical power 60. The system may be housed in one or more convenient housings, represented schematically by dotted line 59.

The elongate dilution chamber or tunnel 20 is for combining vehicle exhaust with ambient air at a constant flow rate, in which the flow rate is controlled by a combination of a fixed orifice plate 22 and a fixed flow rate pump 24. The dilution tunnel 20 comprises a two inch diameter stainless steel pipe. The pump 24 corresponding with the dilution chamber 20 in turn may be controlled by the system control computer 50 to provide a constant flow rate of the exhaust through the plate 22. The tunnel 20 receives a portion of the raw exhaust being emitted through the vehicles tailpipe through a probe 15 including sampling line 16 that has been placed into an exhaust tailpipe of the vehicle, generally indicated by reference numeral 11, the raw exhaust being produced from a vehicle engine 12. The probe 15 comprises a ¼ inch stainless steel tube with a 90° elbow resulting in the opening facing directly upstream into the exhaust stream flow.

A relatively small portion of the raw exhaust in drawn into the sampling line 16 of the probe 15. The sampled portion is passed through a temperature controlled line 17 controlled by a temperature controller 18 and into the dilution tunnel 20. Positioned upstream at the orifice plate 22 is a mixing tee generally indicated by numeral 27 where dilution air is pumped into the stream of raw exhaust that is drawn into the tunnel from the probe in the tailpipe 11. The dilution air provided to the tunnel may be controlled through a proportional solenoid valve 28 connected to a fixed flow rate pump 29 which draws in ambient air to be transferred through to the tunnel. The dilution air volume flow rate is controlled by the proportional solenoid valve 28 is connected to the system control computer 50 and updated every second. The dilution air flow rate is measured by LFE 42. The instantaneous volume flow rate is inversely proportional to the ratio of the engine air inlet volume flow rate at that time and the engine inlet air flow rate at idle.

The tunnel 20 exhausts the bulk of the diluted exhaust through outlet line 32. Within line 32 are provided a particulate filter 34 and a mass flow controller 36.

Maximum dilution within the dilution tunnel occurs at engine idle. The total dilute exhaust rate flow and the dilution air are controlled by the system computer through a mass air flow controller and the proportional solenoid valve respectively. The raw exhaust flow into the dilution tunnel and the dilution ratio can be set by adjusting these two components.

Another form of measurement used in the present invention is to use laminar flow elements (LFE) which provide for the precise and accurate measurement of air flow using a pressure differential across a matrix which ensures that the airflow is laminar. The pressure differential across the matrix results in an airflow volume over time. As such an LFE 40 can be used for the measurement of the engine air inlet and the dilution air pumped to the mixing tee. Differential pressure transducers 41 record the pressure differences across the LFE matrices. Additionally, thermocouples may be used to record the exhaust stream and the dilution air temperatures.

At a predetermined position within the tunnel or chamber 20 for example, a distance equal to ten times the orifice diameter, from the orifice plate 22, a plurality of sampling probes 70, 72, 74 respectively is positioned such that the opening of each probe faces into the flow of the dilute stream exhaust. The probes 70, 72, 74 located in the tunnel include a series of tube-type sampling probes, i.e., three, ¼ inch stainless steel tube sampling probes. Connected to the probes 70, 72, 74 are mass flow controllers, 80, 82, 84 respectively which in turn are connected to low flow rate pumps 91, 93, 95. Samples of dilute exhaust are therefore able to be drawn from the tunnel 20 into and through the probes 70, 72, 74 using low rate pumps 91, 93, 94 respectively. One or more of the sampling media may be linked to one or more analyzers, which in turn deliver emissions component data to the controller 50.

The dilute exhaust, which is directed to a sample media holder for the determination of an average sample over a prescribed cycle or engine operation. The system has the capability to collect simultaneously various emission components including THC, CO, Nox, CO2 using a TEDLAR (™) bag, aldehydes and ketones with a 2, 4-DNPH prepared cartridge, semi-volatile organic compounds using a TENAX (™) cartridge, and light hydrocarbon compounds using a second TEDLAR™ bag. Polyurethane foam plugs within a canister may be used in place of one of the other sample media listed above if PAH and n-PAH are required.

After completion of sampling, the sample media may be removed for analyses. Modal analyses may be determined for a host of compounds by means of continuous emissions monitor (CM) connected to one of the dilution tunnel probes. The output from the CM may be connected to the system computer for continuous data collection and data processing at the conclusion of the tests or in real time. The host computer will calculate the emissions mass rate per second or will determine an integrated emissions rate.

Particulate mass is preferably determined gravimetrically using 70 mm filters. A filter holder is located at the outlet of the dilution tunnel in order to ensure that the entire volume of dilute exhaust passes through the filter.

The sampling system is provided with a control system 50, for example as a system control computer, which is adapted to allow a user to input instructions and to receive output from the system. The system control computer 50 allows for the receiving and recording of data from the sensors, and to control the various functions, for example controlling the mass flow rate of the dilute samples, based on an adjustable parameter in the controlling software.

The computer-driven system controller 50 may record on a continuous basis engine air inlet volume, exhaust temperature, engine RPM, and engine torque may also be input. For this purpose, engine air inlet volume is preferably measured using a laminar flow element (or a series of hot wire anemometers) exhaust temperatures measured via a thermocouple. Engine RPM is preferably measured by way of a Hall Effect sensor. The data from these inputs may be used for data acceptance and verification by plotting the results after completion of identical cycles to verify repeatability of speed and engine load analysis. The control system 50 may be programmed to record engine output data on a continuous basis or to record an average of the output data for a selected duration or engine cycle such as a running of the engine between an idle speed to full power output.

The pressure transducers used for the measurement of barometric pressure and the air flow through the laminar flow elements provide the system with the capability to operate in higher altitudes by compensating for the reduced air pressure.

In an example of a use of the system described above, the sampling system may be mounted on a vehicle with a portable generator to provide electrical power. A probe is mounted in the vehicle's exhaust pipe and connected to a heated sample line to draw the sample into the dilution tunnel. A mass air flow sensor is connected to the air inlet of the engine to record air flow rates. A thermocouple is placed in the exhaust pipe to measure exhaust temperature and a Hall Effect sensor is connected to the engine for recording engine RPM. A portable computer is connected to the sample system, programmed to record all of the parameters noted above and to set and record the test system parameters, in particular to control the pressure transducers, mass flow controllers, laminar flow elements, and proportional valves. The computer further calculates the emission mass rates per second for the various emission components measured by the system, or will calculate an integrated emissions rate.

Additionally, quick connects or the like may be located in the sampling line of any of the three probes to allow for the placement of various forms of sample media holders for analyzers 90, 92, 94 for non-regulated emissions including volatile and semi-volatile organic compounds, carbonyls, PAH (polycyclic aromatic hydrocarbons) and n-PAH (nitrated PAH) and other selected target compounds.

In an alternative embodiment, for a continuous measurement of the regulated exhaust emissions, a separate sample is drawn from the tunnel using a fourth sample probe 100 (as illustrated in FIG. 3). The sample is directed to a self contained exhaust emissions analyzer 102. Using the continuously recorded emissions analyzer data, engine air inlet volume, exhaust temperature, and engine RPM, the emissions mass rate is determined for each second of operation. Integrating this data over the cycle provides a mass emissions number or average emissions mass rate.

For reasons of simplicity, the air flow through the field sampling system will be described in sequence as it is produced and measured from a vehicle under a load.

The air flow drawn through the engine 12 under test may first be measured from a LFE engine inlet air measure, which may be directly linked to the system control computer. As the engine produces exhaust, and the raw exhaust exits through the vehicle's tailpipe 11 or pipes, a portion of the exhaust is drawn through a probe 15 or the like (i.e. sampling line 16) through which the raw exhaust passes through a temperature controlled line 17 to the dilution tunnel or emissions dilution chamber 20 for analysis.

If desired, a portion of the raw exhaust may be drawn from the sampling line prior to the temperature controlled portion of the sampling line for analyzation or measurement, from which the data may be transferred to the system control computer.

As engine and/or vehicle exhaust enters into the dilution chamber or tunnel for sample collection, ambient dilution air passes through a device as a LFE for flow rate measurement and subsequently into a mixing tee coupled to the dilution tunnel 20 upstream of a plate having a predetermined orifice size. As the air flow passes through the chamber drawn by suitable means; i.e., such as a fixed flow rate pump, a portion of the stream of diluted raw exhaust is drawn into the series of probes located within the tunnel or chamber downstream of the orifice plate. The probes, controlled by mass flow controllers and suitable pump means, draw a portion of the stream to be analyzed by suitable analyzers, for example analyzers 1 through 3.

The system operates on a principle of partial flow whereby a small volume of the raw exhaust from the source engine is drawn into the dilution tunnel 20 for mixing with a controlled volume of ambient air. Proportional samples of a dilute sample exhaust are then collected for measurement of both regulated and non-regulated emissions, enabling an accurate and complete characterization of the emissions emitted by the source engine.

The controller includes a software-driven processor comprising the process controls necessary for operation of the system to carry out transient testing while a vehicle or other test engine is being used under "in use" conditions. In addition, the software contains engineering support programs to ensure that the system operates as designed and as contemplated doing field-testing. The software thus includes:

a system to conduct static simulation testing for troubleshooting and system flow verification;

a system to carry out quality control techniques for the verification of sample system dilution and sampling;

a system for confirmation and adjustment of tunnel main flows to optimize the system for engine displacement;

a system for compensation for changes in altitude;

a system for calculation of mass emissions; and the ability to accept incorporation of a second dilution tunnel 20 for increased dilute exhaust flow rates.

The logic control for the fixed sampling system will be described in sequence.

The system control computer 50 provides input and output commands for the data collection and acquisition. The control system receives data from the LFE engine inlet air and the LFE dilution air, such as flow rates, temperature and pressure which is then stored and utilized by the controlling software. The raw exhaust emissions analyzer 30 may also be directly connected to the control system computer, which provides for the continuous measurement or analysis of the raw exhaust. With information based on the stored information from the LFE sources, the control system provides flow rate adjustment to the proportional solenoid valve which provides the ambient air flow to the dilution tunnel or chamber.

In addition, the control system regulates the mass flow controllers, and receives data in turn to control the pumps which draw the samples through the sampling lines associated with each controller.

Data received from the various sources may then be used to provide a user to perceive the exhaust emissions information, for example the emission concentrations, total dilute exhaust volume and other pertinent information.

A method of interest of using the embodiment shown at FIGS. 1 and 2 for measurement of vehicle exhaust emission components is to associate the system with a means for measuring other engine or vehicle performance parameters such as engine torque. With such a measurement in hand, emissions data in 2/BHp-hr may be determined. Torque may be measured by means of a portable dynamometer and analyses bench, to provide a complete portable exhaust emissions system. Such a system provides the flexibility for testing vehicles in a variety of non-conventional locations, and to replace the standard proportional volume sampling system (referred to as the CVS) normally found in vehicle exhaust emissions testing laboratories and light duty vehicle inspection and maintenance (I–M) emissions stations.

Although preferred embodiments of the invention have been described above, this invention is not limited to the particular parameters and features described in detail herein. It will be apparent to those skilled in the art that numerous modifications form part of the present invention insofar as they do not depart from the scope of the appended claims.

What is claim is:

1. In a portable self-contained system for sampling and analysing engine exhaust emissions of a mobile or stationary emission source in which the system has an inlet pipe for receiving an emission sample, a dilution tunnel having a plurality of sampling probes within said dilution tunnel for withdrawing controlled volumes of diluted engine exhaust upstream from said dilution tunnel, emissions analysing means downstream of said tunnel, control means for introducing dilution air into said tunnel, a sampling probe upstream of said dilution tunnel in operative association with said control means, characterized by:

air inlet measuring means measuring air inlet flow rate into an engine, a plurality of pump means with which to draw a sample of said diluted engine exhaust through said probe means, and control means comprising a variable controller for controlling the volume of dilution air of said exhaust in inverse proportion to the ratio of engine air inlet flow rate and the engine inlet air flow rate at engine idle.

2. The system as defined in claim 1, wherein said engine air inlet measuring means comprises laminar flow elements.

3. The system as defined in claim 1, comprising means for collecting and concentrating a plurality of emission samples for measuring specific emissions selected from one or more of:

THC;
CO;
$NO_x$;
$CO_2$;
aldehydes;
ketones;
semi-volatile organic compounds;
volatile organic compounds;
PAH;
n-PAH; and,
particulates.

4. The system as defined in claim 1, said control means further comprising means for integrating data over an engine cycle of an engine ranging from idle to full engine load, said data comprising emissions mass number or average emissions mass rate, engine air inlet flow rate, exhaust temperature, and engine RPM.

5. The system as defined in any one of claims 1 to 4, further comprising means for collecting and concentrating emission samples with sampling media selected from one or more of:

TEDLAR™ bag;
2, 4-DNPH prepared cartridge;
TENAX™ cartridge; and,
polyurethane foam.

6. The system as defined in claim 1, wherein the volume of exhaust drawn from the emission source is varied.

7. In a method for sampling and analysing engine exhaust emissions from a stationary or mobile emission source in a portable self-contained system having a volume of exhaust drawn from said emission source, including the steps of:

connecting said portable self-contained system to said mobile or stationary emission source;
drawing a portion of engine exhaust emissions into a dilution tunnel upstream from said dilution tunnel during operation of said emission source; characterized by:
measuring the air intake flow rate from an engine during operation;
diluting said engine exhaust emissions in inverse proportion to the ratio of engine air inlet flow rate of said engine during an analysing event and engine air inlet flow rate of said engine during idle;
collecting samples of said diluted exhaust emission with a plurality of sampling probes; and,
analysing emission mass rates for one or more emission component being measured.

8. A method as defined in claim 7, further comprising measuring and recording parameters selected from one or more of: engine inlet mass air flow rate, engine exhaust temperature, engine RPM, engine torque, and speed.

9. A method as defined in claim 8, further comprising analysing one or more of: continuous mass number, average emissions mass rate, engine air inlet flow rate, exhaust temperature, and engine RPM during operation of said emission source.

10. A method as defined in claim 9, further comprising sampling diluted exhaust with a plurality of probes each having an inlet within said dilution tunnel and delivering diluted exhaust samples to a plurality of collection media for concentrating selected emission components.

11. A method as defined in claim 10, further comprising measuring emission components selected from one or more of:

THC;
CO;
$NO_x$;
$CO_2$;
aldehydes;
ketones;
semi-volatile organic compounds;
volatile organic compounds;
PAH;
n-PAH; and,
particulates.

12. A method as defined in claim 7, further comprising analysing one or more of: mass number, average emissions mass rate, engine air inlet flow rate, exhaust temperature, and engine RPM during operation of said emission source.

13. A method as defined in claim 7, further comprising sampling diluted exhaust with a plurality of probes each having an inlet within said dilution tunnel and delivering diluted exhaust samples to a plurality of collection media for concentrating selected emission components.

14. A method as defined in claim 7, further comprising measuring emission components selected from one or more of:

THC;
CO;
$NO_x$;
$CO_2$;
aldehydes;
ketones;
semi-volatile organic compounds;
volatile organic compounds;
PAH;
n-PAH; and,
particulates.

15. A method as defined in claim 8, further comprising sampling diluted exhaust with a plurality of probes each having an inlet within said dilution tunnel and delivering diluted exhaust samples to a plurality of collection media for concentrating selected emission components.

16. A method as defined in claim 8, further comprising measuring emission components selected from one or more of:

THC;
CO;
$NO_x$;

$CO_2$;
aldehydes;
ketones;
semi-volatile organic compounds;
volatile organic compounds;
PAH;
n-PAH; and,
particulates.

17. A method as defined in claim 9, further comprising measuring emission components selected from one or more of:
THC;
CO;
$NO_x$;
$CO_2$;
aldehydes;
ketones;
semi-volatile organic compounds;
volatile organic compounds;
PAH;
n-PAH; and,
particulates.

18. The system as defined in claim 1, wherein said volume is varied by the mass air flow rate controller at the exit of said tunnel and the volume of dilution air directed into said tunnel.

19. the system as defined in claim 1, wherein said volume is varied by the mass air flow rate controller at the exit of said tunnel or the volume of dilution air directed into said tunnel.

20. The method as defined in claim 7, wherein said volume is varied by the mass air flow rate controller at the exit of said tunnel and the volume of dilution air directed into said tunnel.

21. the method as defined in claim 7, wherein said volume is varied by the mass air flow rate controller at the exit of said tunnel or the volume of dilution air directed into said tunnel.

* * * * *